(12) United States Patent
Monkam Nitcheu

(10) Patent No.: US 11,918,591 B2
(45) Date of Patent: Mar. 5, 2024

(54) PHARMACEUTICAL COMPOSITION FOR INHIBITING THE INFECTIVITY OF LIPID BILAYER VIRUSES, TREATING ASSOCIATED DISEASES AND THEIR COMPLICATIONS

(71) Applicant: Guy Faustin Monkam Nitcheu, Lille (FR)

(72) Inventor: Guy Faustin Monkam Nitcheu, Lille (FR)

( * ) Notice: Subject to any disclaimer, the term of this patent is extended or adjusted under 35 U.S.C. 154(b) by 0 days.

(21) Appl. No.: 17/700,547

(22) Filed: Mar. 22, 2022

(65) Prior Publication Data

US 2022/0305029 A1    Sep. 29, 2022

(30) Foreign Application Priority Data

Mar. 27, 2021 (FR) ....................................... 2103144

(51) Int. Cl.
*A61K 31/56* (2006.01)
*A61K 31/015* (2006.01)
*A61K 31/11* (2006.01)
*A61K 45/06* (2006.01)

(52) U.S. Cl.
CPC ............. *A61K 31/56* (2013.01); *A61K 31/015* (2013.01); *A61K 31/11* (2013.01); *A61K 45/06* (2013.01)

(58) Field of Classification Search
CPC ..................................................... A61K 31/56
See application file for complete search history.

(56) References Cited

FOREIGN PATENT DOCUMENTS

FR        3061658        *    7/2018

OTHER PUBLICATIONS

Janjira et al. CAS: 147: 439535, 2007.*

* cited by examiner

*Primary Examiner* — Rei Tsang Shiao
(74) *Attorney, Agent, or Firm* — Rivka Friedman

(57) ABSTRACT

This invention related to a pharmaceutical composition which can be used as an anti-infective on enveloped pathogens and their various complications.

7 Claims, No Drawings

PHARMACEUTICAL COMPOSITION FOR INHIBITING THE INFECTIVITY OF LIPID BILAYER VIRUSES, TREATING ASSOCIATED DISEASES AND THEIR COMPLICATIONS

This invention relates to a pharmaceutical composition that can be used as an anti-infective on enveloped pathogens, in particular coronaviruses, and their various complications.

BACKGROUND ART

Covid-19 is a pandemic of an emerging infectious disease, called Covid-19, caused by the SARS-CoV-2 coronavirus. The pathogenesis of Covid-19 is very heterogeneous and infected individuals do not necessarily develop symptoms. The most common manifestations noted in the literature are the classic signs of a respiratory infection: fever, cough, respiratory discomfort due to accumulation of fluid in the bronchioles. Other less systematic signs, which vary according to age, include headaches, malaise, repeated falls or confusion, nasal congestion, sore throat, nausea, vomiting, diarrhea, loss of taste, loss of smell, erythema, rash, and less commonly, frostbite.

The treatment of the disease aims at alleviating the symptoms: Analgesics such as paracetamol and anti-diarrhea drugs for fever and diarrhea, rest for the duration of the infection, hydration with water to avoid dehydration due to fever and aches. Furthermore, oxygen therapy, thrombosis prevention, anti-arrhythmics, anticoagulants or dialysis can be implemented in addition to symptomatic treatments.

In addition, many projects are under way to better understand the virus and the disease it causes, and to identify new therapeutic targets. This allowed to set new therapeutic strategies:

Vaccination: The arrival of Covid-19 vaccines is providing a surge of hope in the fight against SARS-CoV-2 infection. But what about the efficacy of vaccines on SARS-CoV-2 and its variants in the long term?

Plasma therapy: It consists in extracting plasma from recovered patients and administering it to those who are seriously ill in a manner similar to a vaccine.

Immunotherapy: The goal is to use antibody-based drugs to prevent hospitalization of patients at risk of developing severe forms of Covid-19, particularly in those with co-morbidities such as cardiovascular disease, chronic respiratory disease, obesity, diabetes, chronic renal failure, and HIV- or cancer-related immunosuppression. However, many questions about immunogenicity, specificity, safety, and therapeutic potential remain unanswered.

Today, there is no infectious treatment that can solely cure Covid-19. The use of immunostimulants, antivirals and antioxidants may help reduce the risk of Covid-19.

In this infectious context, the cell membrane plays a major role in a large number of physiological or pathophysiological processes. Indeed, it contains most of the essential elements for exchanges between the cell and its environment. It is made up of micro-domains also called rafts. These are made up of a compact assembly of lipids (glycosphingolipids and/or sphingomyelin and cholesterol) and proteins (glycosylphosphatidylinositol-anchored proteins, cholesterol-bound proteins, transmembrane proteins, double acetylated Src-family tyrosine kinases, alpha-subunits of heterotrimeric G proteins). Cholesterol plays a role of dynamic "glue" which gives rigidity and structures these micro-domains. These proteins, including ACE2, TMPRSS2 and many other receptors, play a key role in cell signaling and are involved in some inflammatory and infectious processes, and in the development of metabolic disorders and carcinogenesis. In addition, the dysfunction or structural changes that accompany the activation of this membrane by pathogens or endogenous signals can be the cause of an overproduction of microparticles contributing to the amplification of inflammation, systemic immune hyperactivation, susceptibility to coagulation, initiation, progression, and aggravation of cardiovascular pathologies, including atherosclerosis, myocardial infarction, stroke, and cancer.

Viral inflammation is thought to account for a significant portion of disorders of the metabolic syndrome, particularly in SARS-CoV-2 infected subjects.

Furthermore, d-limonene is known for its antiseptic, and antiviral potential. It also has anti-diabetic and hypolipidemic properties and can therefore be considered as a potential agent to prevent and treat metabolic disorders routinely encountered in infectious diseases. Its antioxidant, anti-inflammatory and anti-cancer properties are known. In humans, d-limonene has shown low toxicity after a single dose, repeated over a year.

Beta-sitosterol and lupeol are phytosterols with a molecular structure similar to that of cholesterol. In that respect, they can compete with the latter. Their roles in plants are identical to that of cholesterol in humans, namely, to maintain the structure and function of the cell membrane. Numerous scientific data have shown that these sterols have hypoglycemic, hypolipidemic, anti-inflammatory, antipyretic, immunostimulant and anticancer properties. They can inhibit SARS-CoV-2 entry into cells by limiting the adhesion of the Spike protein to the ACE2 receptor. Their pharmacological potential makes them therapeutic agents in metabolic syndrome disorders and infections by lipid bilayer pathogens.

Cinnamaldehyde is known for its hypoglycemic, hypolipidemic and anticancer properties.

Its antibacterial, antifungal, immunostimulant, and antiviral properties are known.

TECHNICAL PROBLEM TO BE SOLVED

A purpose of this invention is to offer a novel pharmaceutical composition suitable for use as a medicine and more particularly suitable for use in the treatment of infections by enveloped pathogens, the diseases they cause, and their complications.

Another purpose of the invention is to offer a new pharmaceutical composition usable as a medicine and more particularly usable in the treatment of diseases which remedies all or part of the disadvantages associated with the compositions of the background art mentioned above.

Another purpose of the invention is to offer a pharmaceutical composition usable as a medicine, in particular for the therapeutic treatment of diabetes, dyslipidemia and obesity.

Another purpose of the invention is to offer a pharmaceutical composition that inhibits the inflammatory phenotype of circulating monocytes, macrophages, white blood cells, and pancreatic cells in patients with comorbidities.

Another purpose of the invention is to offer a pharmaceutical composition that will reduce or even inhibit the entry of pathogens (viruses, bacteria, parasites, etc.) into their target cells.

Another purpose of the invention is to offer a pharmaceutical composition that limits or even inhibits the infectivity of SARS-CoV-2 and different variants in cells, inhibits viral replication, and activates an appropriate immune response.

Another purpose of the invention is to provide a pharmaceutical composition, particularly as mentioned above, which has reduced toxicity and/or is well tolerated by patients.

BRIEF DESCRIPTION OF THE INVENTION

In order to solve at least one of the technical problems mentioned above, this invention proposes a pharmaceutical composition, which characteristically according to the invention, comprises as active ingredient a combination of d-limonene, lupeol, beta-sitosterol, cinnamaldehyde, and possibly epicatechin, curcumin and their combinations.

The Applicant has indeed found that such a pharmaceutical composition was active in viral, bacterial, fungal, and parasitic infections.

The Applicant has also demonstrated a synergistic effect that provides an enhanced action of the composition of the invention on the diseases referred to in the Background Art, characterized by the inhibition of the entry of pathogens into the host cells, by the inhibition of chronic inflammation and systemic immune hyperactivation.

The Applicant also found that the composition according to the invention had a preventive effect on the various complications related to COVID-19.

DETAILED DESCRIPTION

The pharmaceutical composition according to the invention can be used as a medicine, and more specifically for its use in the preventive and curative treatment of enveloped pathogen infections and their various complications.

Based on a specific making of the invention, its composition can further comprise a mixture of d-limonene, lupeol, b-sitosterol, cinnamaldehyde; or a mixture of d-limonene, lupeol, b-sitosterol cinnamaldehyde and Epigallocatechin Gallate (EGCG); or a mixture of d-limonene, lupeol, b-sitosterol, cinnamaldehyde and curcumin; or a mixture of d-limonene, lupeol, b-sitosterol, cinnamaldehyde, Epigallocatechin Gallate (EGCG) and curcumin.

As an example, it can comprise, as a weighted percentage of the total mass of active ingredients, a percentage by weight of d-limonene substantially equal to or higher than 10% and substantially equal to or lower than 55, and in particular substantially equal to or higher than 20% and substantially equal to or lower than 40%;

a percentage of lupeol substantially equal to or higher than 15% and substantially equal to or lower than 55%, and in particular substantially equal to or higher than 30% and substantially equal to or lower than 40%;

a percentage of beta-sitosterol substantially equal to or higher than 10% and substantially equal to or lower than 45%, and in particular substantially equal to or higher than 15% and substantially equal to or lower than 30%;

a percentage of cinnamaldehyde substantially equal to or higher than 15% and substantially equal to or lower than 45%, and in particular substantially equal to or higher than 20% and substantially equal to or lower than 40%;

a percentage of Epigallocatechin Gallate (EGCG) substantially equal to or higher than 15% and substantially equal to or lower than 40%, and in particular substantially equal to or higher than 25% and substantially equal to or lower than 35%;

a percentage of Curcumin substantially equal to or higher than 15% and substantially equal to or lower than 40%, and in particular substantially equal to or higher than 25% and substantially equal to or lower than 35%.

The composition of the invention further comprises at least one pharmaceutically acceptable excipient. The excipient can be solid or liquid. It can be selected, for example, among purified water, ethyl alcohol, propylene glycol, glycerin, vegetable oils, animal oils, hydrocarbons, silicones, sugars such as glucose, cyclodextrin, levulose, wheat starch, corn starch, potato starch, xanthan gum, acacia gum, tragacanth gum, Sterculia gum, Guar gum, or "Guaranates", pectins, alginates, carrageenan, agar or Agar-Agar, gelatin, cellulose, and its derivatives.

The composition of the invention can be administered by any suitable route, for example oral, rectal, local (e.g., topical), intraperitoneal, systemic, intravenous, intramuscular, subcutaneous, or mucosal, especially sublingual, or using a patch, or in encapsulated or immobilized form on liposomes, microparticles, microcapsules, associated with nanoparticles and the like. Non-limiting examples of excipients suitable for oral administration include talc, lactose, starch and its derivatives, cellulose, and its derivatives, cyclodextrin, piperine, polyethylene glycols, acrylic acid polymers, gelatin, magnesium stearate, animal, vegetable or synthetic fats, paraffin derivatives, glycols, stabilizers, preservatives, antioxidants, wetting agents, anti-caking agents, dispersants, emulsifiers, taste modifiers, penetrating agents, solubilizing agents. The techniques of formulation and administration of drugs and pharmaceutical compositions are well known in the technique considered here, the skilled person being able to refer in particular to the book Remington's Pharmaceutical Sciences, latest edition.

Based on the invention, the composition can advantageously be administered orally, or intravenous injection.

Advantageously, the composition according to the invention is suitable to be administered orally or intravenously at a dose equal to or higher than 40 mg/kg/24 h and equal to or lower than 200 mg/kg/24 h in one or more doses to a mammal with such a need.

As an example, the composition of the invention may be used in the preventive and/or curative treatment of an infection caused by an enveloped pathogen.

The composition according to the invention can advantageously be used in the treatment of chronic inflammatory disease and/or resulting from carbohydrate imbalance and/or lipid imbalance and/or cellular cholesterol transporter dysfunction and/or severe acute respiratory syndrome and/or systemic immune hyperactivation, in particular in patients infected with an enveloped pathogen and comorbidities.

In the case of infection by a pathogen with a lipid bilayer envelope, for example SARS-Cov-2, the Applicant has shown that the composition according to the invention gave good results at least in vitro and showed low cytotoxicity.

The mechanism of action of the composition of the invention is not fully elucidated. It is more than likely that it acts simultaneously on various mechanisms responsible for the diseases mentioned in the Background Art. It is thought to function by a synergistic regulatory effect on nuclear receptors, in particular PPARs, LXRs and RXRs, thus allowing the efflux of cellular and membrane cholesterol, the inhibition of the overexpression of some sphingolipids, in particular glycosphingolipids, of some membrane proteins, in particular ACE2, and the inhibition of the production of pro-inflammatory cytokines. It is also believed to act through an immunostimulant effect.

Furthermore, the composition according to the invention de-structures, and restructures the lipid composition of the cells, and in particular of the membrane lipid rafts, targets of the enveloped pathogens, and could therefore prevent the stabilization of these microdomains, the setting up of a fusion complex, the formation of synapses, the endocytosis, and thus in the long run, the penetration of these enveloped pathogens into the cells.

Furthermore, the modification of the lipid composition of these membrane microdomains causes a conformational change, an alteration of the functional or dysfunctional activity of the proteins found within, in particular the virus entry receptors, the G-protein coupled receptors and ultimately an alteration of cell signaling pathways involved in many pathophysiological processes, including pathogen-induced infections, cancer, obesity, metabolic diseases, autoimmune diseases, and neurodegenerative diseases.

This lipid disorganization could also occur in the envelope of pathogens and would then modify the conformation of information proteins involved in the infection process, their binding to their target cells. This mechanism is thought to apply to viruses, bacteria having biophysical and biochemical properties similar to their target cells, particularly at the level of the lipid bilayer envelope.

The composition according to the invention can advantageously be used to decrease or inhibit drug resistance of pathogens and their variants, inflammatory phenotype of cells, oxidative stress, senescence of immune cells, and to increase an innate and adaptive immune response.

In addition, the composition according to the invention can be used in the treatment of infections caused by enveloped pathogens and their variants, in particular coronaviridae (SARS-CoV, MERS-CoV, SARS-CoV-2), herpes pesviridae (Herpes simplex, Varicella zoster, EBV, HHV-6 to 7, Monkey Herpes B), retroviruses (lentiviruses including HIV-1 and HIV-2, oncoviruses, and spumaviruses), myxoviruses, paramyxoviridae (para-influenza, mumps, measles, Respiratory Syncytial Virus), rabies virus, Lassa virus, hantavirus, Marburg virus, rubella virus, and in the treatment of cancers.

These include Kaposi's sarcoma, Burkitt's lymphoma, immunoblastic lymphoma, brain lymphoma, primary, non-Hodgkin's malignant lymphomas (NHML), cervical cancer, oral cancer, stomach cancer, colon cancer, especially invasive colon or colorectal cancer, rectal cancer, anal cancer, liver cancer, hepatocellular carcinoma, gallbladder cancer, pancreatic cancer, lung cancer, in particular adenocarcinoma of the lung, leukemia in the chronic or acute form, multiple myeloma, Hodgkin's lymphoma, tumors of the brain and others in the nervous system, bladder cancer, ovarian cancer, uterine cancer, testicular cancer, kidney cancer, prostate cancer and breast cancer, especially those associated with fatty tissue, bone tumors.

This invention also relates to a pharmaceutical preparation which comprises the composition according to the invention, and, in addition, in admixture or separately packaged at least one anti-inflammatory agent and/or antidiabetic agent and/or lipid-lowering agent and/or anti-infective agent and/or anticancer agent for use in the therapeutic treatment of infections caused by pathogens and their complications, simultaneously, sequentially or spaced in time.

For example, the anti-diabetic agent may be selected from among biguanides, hypoglycemic sulfonamides and glinides, alpha-glucosidase inhibitors, incretins including GLP-1, insulin, the lipid-lowering agent may be selected from statins, fibrates, ezetimibe, nicotinic acid, cholestyramine, the antiviral agent may be selected from nucleoside or non-nucleoside reverse transcriptase inhibitors, protease inhibitors, fusion inhibitors and integrase inhibitors, the anticancer agent may be selected from anti-metabolites (methotrexate, capecitabine, 5-fluorouracil), alkylating agents (cisplatin, mitomycin c, busulfan) and related agents (melphalan, chloraminophen, cyclophosphamide), compounds acting on the mitotic spindle (vinblastin[1], vincristine, docetaxel), tyrosine kinase inhibitors (afatinib, erlotinib, sunitinib), threonine kinase inhibitors (vemurafenib, everolimus, temsirolimus), agents acting on topoisomerase (daunorubicin, doxorubicin, etoposide), proteasome inhibitors, DNA methyltransferase inhibitors, histone deacetylase inhibitors, immunomodulators (interferons, corticoids, talimogene), monoclonal antibodies (cetuximab, gemtuzumab, trastuzumab, bevacizumab, rituximab), some genetically modified viruses that preferentially target cancer cells, gluthation, vitamin C, calcium folinate and their mixtures, and in particular the mixture of two of the said anticancer agents, radioactive agents suitable for brachytherapy and/or injectable or ingestible active metabolites.

This invention also relates to a pharmaceutical preparation which comprises d-limonene, lupeol, beta-sitosterol, cinnamaldehyde and optionally epicatechin, curcumin and their mixtures in combination.

This invention also relates to a dietary supplement which comprises in combination d– limonene, and/or lupeol, and/or beta-sitosterol, and/or cinnamaldehyde, and/or epicatechin, and/or curcumin.

DEFINITIONS

The term "therapeutic treatments" refers to curative and prophylactic treatment; within the meaning of the invention, a therapeutic treatment at least partially restores, at least partially corrects, or at least partially modifies physiological functions by exerting a pharmacological, immunological, or metabolic action.

The term "patient" refers to an animal or human mammal. The composition according to the invention can also be used in veterinary medicine.

The term "patients with diabetes" refers to patients with type 1 diabetes, patients with type 2 diabetes, female patients with gestational diabetes, patients with diabetes insipidus, and patients with renal diabetes.

The term "dyslipidemia" refers to hyperlipidemia and hypolipidemia as determined by current criteria.

The term "inflammation" refers to a set of reactions triggered by the body in response to an aggression suffered. This can be of external origin such as an injury, an infection, a trauma, or from within the body itself as in autoimmune diseases.

Within the meaning of this invention, an "anti-cancer agent" is an element exhibiting at least in vitro action against cancer cells, regardless of its mechanism of action. Within the meaning of this invention, "action" means the destruction or at least partial modification of cancer cells which makes it possible, in particular, to limit the proliferation of cancer cells and/or their spread.

The term "infection" refers to the invasion of a living organism by germs, more precisely pathogenic microorganisms such as a bacterium or a virus, requiring a host, most often a cell, the components of which it uses to multiply.

As used in this invention, a "dietary supplement" is a foodstuff whose purpose is to supplement the normal diet, and which is a concentrated source of nutrients or other substances having a nutritional or physiological effect alone or in combination.

With respect to the anti-inflammatory agent and/or anti-diabetic agent and/or lipid-lowering agent and/or anti-infective agent and/or anti-cancer agent mentioned, the terms used include, unless otherwise indicated, the constitutional isomers, conformational stereoisomers, enantiomers and diastereomers of the chemical compound considered.

With respect to cinnamaldehyde (CA) in the composition according to the invention, the term encompasses, unless otherwise indicated, its derivatives, in particular 2-hydroxycinnamaldehyde (HCA), 2'-benzoyloxycinnamaldehyde (BCA), the dimers of formation, in particular HCA-HCA, BCA-BCA, CA-CA.

With respect to epicatechin in the composition according to the invention, the term encompasses, unless otherwise indicated, its derivatives including catechin, gallocatechin (GC), epicatechin gallate (ECG), epigallocatechin (EGC), epigallocatechin gallate (EGCG).

With respect to curcumin in the composition according to the invention, the term includes, unless otherwise indicated, its various synthetic analogues.

EXAMPLES

The percentage of the compositions below is a percentage by mass in relation to the total mass of the active ingredients.

Composition 1a: d-limonene (50%), lupeol (20%), b sitosterol (20%), cinnamaldehyde (10%).

Composition 1b: d-limonene (40%), lupeol (20%), b sitosterol (30%), cinnamaldehyde (10%).

Composition 2a: d-limonene (40%), lupeol (10%), b sitosterol (10%), cinnamaldehyde (10%), EGCG (30%).

Composition 2b: d-limonene (50%), lupeol (10%), b sitosterol (10%), cinnamaldehyde (10%), EGCG (20%).

Composition 3a: d-limonene (40%), lupeol (10%), b sitosterol (10%), cinnamaldehyde (10%), curcumin (30%).

Composition 3b: d-limonene (50%), lupeol (10%), b sitosterol (10%), cinnamaldehyde (10%), curcumin (20%).

EXPERIMENTAL RESULTS

The antiviral activity of the compositions was evaluated in 3 steps on Vero E6/Vero-81 cells: First step: Determination of the cytotoxicity of the 6 molecules and the 3 compositions.

Cytotoxicity will be determined by an MTS assay, based on the bio-reduction of tetrazolium MTS in viable, metabolically active cells in stained formazan, which latter is quantified by measuring the absorbance at 490-500 nm. This amount is proportional to the number of living cells in culture compared to untreated cells. Cell viability is measured after 24 hours of incubation with increasing concentrations of the test preparations.

Second step: Determination of the antiviral activity of high concentration compositions.

The compositions will be tested in triplicates in vitro on Vero E6/Vero-81 cells. The highest non-toxic dose of the preparations will be brought into contact with Vero E6/Vero-81 cells infected with SARS-CoV-2. After 16 hours of incubation at 37° C., the cells will be lysed, and the viral infection will be demonstrated by the revelation of the presence of the SARS-CoV-2 nucleocapsid protein in western blotting. The presence of the nucleocapsid protein will be quantified with Image J software.

Go/No go: If some preparations are found to be non-inhibiting at high concentrations, they will not be included in the third step.

Third step: Determination of the inhibitory concentration 50 (IC50) of preparations The antiviral activity of the compositions will be tested in triplicate in vitro on Vero E6/Vero-81 cells infected with the SARS-CoV-2 Coronavirus. Increasing doses of the compositions will be brought into contact with Vero E6/Vero-81 cells infected with SARS-CoV-2. After 16 hours of incubation at 37° C., the cells will be lysed, and the viral infection will be demonstrated by the revelation of the presence of the nucleocapsid protein in western blotting. The presence of the nucleocapsid protein will be quantified with Image J software. Dose-response curves will be plotted and IC50s determined.

Result: These compositions have low cytotoxicity at acceptable biological concentrations. Significant and positive antiviral activity is also observed for the various combinations against SARS-CoV-2. This pharmaceutical composition can rightly be considered as a drug candidate against COVID-19.

What is claimed is:

1. A pharmaceutical composition comprising:
   d-limonene in the range of 10-55%; lupeol in the range of 15-55%; b-sitosterol in the range of 10-45%; cinnamaldehyde in the range of 15-45%; curcumin in the range of 15-40%; Epigallocatechin Gallate (EGCG) in the range of 15-40% and their mixtures as an active principle.

2. The pharmaceutical composition according to claim 1, characterized as containing, as a weighted percentage of the total mass of the active ingredients,
   a percentage by weight of d-limonene substantially equal to or higher than 20% and substantially equal to or lower than 40%;
   a percentage of lupeol substantially equal to or higher than 30% and substantially equal to or lower than 40%;
   a percentage of beta-sitosterol substantially equal to or higher than 15% and substantially equal to or lower than 30%;
   a percentage of cinnamaldehyde substantially equal to or higher than 20% and substantially equal to or lower than 40%;
   a percentage of Epigallocatechin Gallate (EGCG) substantially equal to or higher than 25% and substantially equal to or lower than 35%;
   a percentage of Curcumin substantially equal to or higher than 25% and substantially equal to or lower than 35%.

3. The pharmaceutical composition according to claim 1 for the preventive and/or curative treatment in need thereof of an infection caused by an enveloped pathogen.

4. The pharmaceutical composition according to claim 3 for treatment of chronic inflammatory disease, and/or resulting from carbohydrate imbalance, and/or lipid imbalance, and/or cellular cholesterol transporter dysfunction, and/or severe acute respiratory syndrome, and/or systemic immune hyperactivation, especially in patients infected with an enveloped pathogen and comorbidities.

5. The pharmaceutical composition according to claim 1, in that it de-structures, and restructures the lipid composition of the cells, in particular of the membrane lipid rafts, changes the composition of the proteins found within, and therefore prevents the stabilization of these microdomains, the penetration of pathogens into cells, the signaling pathways involved in many physiopathological processes, notably in infections, cancer, obesity, metabolic diseases, autoimmune diseases and neurodegenerative diseases.

6. The pharmaceutical composition according to claim 3 for treatment of infections caused by enveloped pathogens and their variants, in particular coronaviridae (SARS-CoV, MERS-CoV, SARS-CoV-2), Herpesviridae (Herpes simplex, Varicella zoster, EBV, HHV-6 to 7, Monkey Herpes B), retroviruses (lentiviruses including HIV-1 and HIV-2, oncoviruses, and spumaviruses), myxoviruses, paramyxoviridae (para-influenza, mumps, measles, Respiratory Syncytial Virus), rabies virus, Lassa virus, hantavirus, Marburg virus, rubella virus and in the treatment of cancers.

7. The pharmaceutical preparation characterized as containing the composition according to claim 1, in addition, in admixture or packaged separately at least one anti-inflammatory agent, and/or anti-diabetic agent, and/or hypo-lipidemic agent, and/or anti-infectious agent, and/or anticancer agent, for the therapeutic treatment of infections caused by pathogens and their complications.

* * * * *